United States Patent [19]

Turner et al.

[11] Patent Number: 6,087,070
[45] Date of Patent: Jul. 11, 2000

[54] PHOTOACTIVATABLE NITROGEN-CONTAINING BASES BASED ON α-AMINO ALKENES

[75] Inventors: Sean Colm Turner, Berkeley, Calif.; Gisèle Baudin, Marly, Switzerland

[73] Assignee: Ciba Specialty Chemicals Corporation, Tarrytown, N.Y.

[21] Appl. No.: 09/039,766

[22] Filed: Mar. 16, 1998

[30] Foreign Application Priority Data

Mar. 18, 1997 [CH] Switzerland ................ 652/97

[51] Int. Cl.$^7$ ............... G03F 7/26; G03F 7/004; G03F 7/027; C07D 237/26
[52] U.S. Cl. ............ 430/280.1; 544/282; 534/752; 534/798; 522/53; 522/50; 522/62; 522/63; 522/65; 522/26; 430/270.1; 430/288.1; 430/285.1; 430/196; 430/325; 430/330; 430/18
[58] Field of Search ............. 544/282; 534/752, 534/798; 522/53, 50, 62, 63, 65, 26; 430/270.1, 280.1, 288.1, 285.1, 196, 325, 330, 18

[56] References Cited

U.S. PATENT DOCUMENTS

| | | | |
|---|---|---|---|
| 4,772,530 | 9/1988 | Gottschalk et al. | 430/138 |
| 5,028,618 | 7/1991 | Seele et al. | 514/333 |
| 5,204,218 | 4/1993 | Kumada et al. | 430/270.1 |
| 5,534,629 | 7/1996 | Desobry et al. | 544/78 |
| 5,545,509 | 8/1996 | Cameron et al. | 430/270.1 |

FOREIGN PATENT DOCUMENTS

| | | |
|---|---|---|
| 0284561 | 9/1988 | European Pat. Off. |
| 3825586 | 2/1990 | Germany |

OTHER PUBLICATIONS

Cameron and Frechet, J. Am. Chem. Soc. (1991) 113, 4303.
Cameron, et al. J. Am. Chem. Soc. (1996) 118, 12925.
Tsunooka, et al. J. Polymer Sci.: Part A:Polymer Chem. (1994), 32, 2177).
Nishikuleo, et al., Polymer. J. (1993) 25, 421.
Nishikuleo, et al., Polymer Sci.: Part A: Polymer Chem. (1993), 31, 3013.
C. Kutal, et al. J. Electrochem. Soc.(1987) 134, 2280.
V. Sreedhara, et al, J. Photochem. Photobiol. A. Chem. 101, (1996), 189.
Synthesis (1993), 659.
Adam et al., Chem. Ber., vol. 122, (1989), pp. 133–143.
Raab et al., Mykosen, vol. 24, No. 8, (1981), pp. 461–470.
Daniil et al., Tetrahedron Letters No. 36, (1977), pp. 3155–3158.
Barluenga et al., J. Org. Chem., vol. 58, (1993), pp. 700–704.

*Primary Examiner*—Cynthia Hamilton
*Attorney, Agent, or Firm*—Luther A. R. Hall

[57] ABSTRACT

The invention relates to organic compounds having a molecular weight of less than 1000 comprising at least one structural unit of the formula (I)

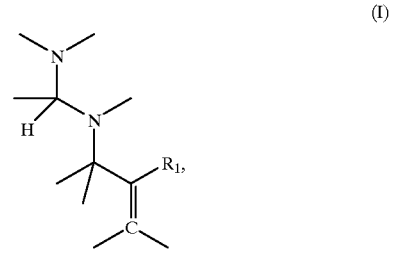

in which
$R_1$ is an aromatic or heteroaromatic radical which is capable of absorbing light in the wavelength range from 200 to 650 nm and in doing so brings about cleavage of the adjacent carbon-nitrogen bond.

The compounds represent photoinitiators for base-catalyzable reactions. Other subjects of the invention are base-polymerizable or crosslinkable compositions comprising compounds having a structural unit of the formula I, a method of implementing photochemically induced, base-catalyzed reactions, and the use of the compounds as photoinitiators for base-catalyzed reactions.

21 Claims, No Drawings

PHOTOACTIVATABLE NITROGEN-CONTAINING BASES BASED ON α-AMINO ALKENES

The invention relates to α-amino alkenes which can be converted photochemically into amidine derivatives, to a process for their preparation and to a process for the photochemical preparation of the amidine derivatives. Further subjects of the invention are base-polymerizable or crosslinkable compositions comprising these α-amino alkenes, a method of implementing photochemically induced, base-catalysed reactions, and the use of the α-amino alkenes as photoinitiators for base-catalysed reactions.

The photolytic generation of bases, and photopolymerization reactions with these bases, have already been described, use being made of various types of photolabile compounds, examples being carbamates (Cameron et al., U.S. Pat. No. 5,545,509 and references cited therein; Cameron and Frechet, J. Am. Chem. Soc. (1991) 113, 4303), α-keto carbamates (Cameron et al., J. Am. Chem. Soc. (1996), 118, 12925), O-acyloximes (Tsunooka et al., J. Polymer Sci.: Part A: Polymer Chem. (1994), 32, 2177), formamides (Nishikubo et al., Polym. J. (1993) 25, 421; idem, J. Polymer Sci.: Part A: Polymer Chem. (1993), 31, 3013), co-amine complexes (C. Kutal et al., J. Electrochem. Soc. (1987), 134, 2280).

The photochemical intramolecular γ-hydrogen elimination reactions of olefins is known but not so well described as the corresponding reactions of carbonyl compounds (cf. V. Sreedhara Rao, A. K. Chandra, J. Photochem. Photobiol. A Chem. 101 (1996), 189 and the references cited therein).

Corresponding thermal reactions of olefins are much better described, for example by J.-L. Ripoll, Y. Vallee in Synthesis (1993), 659 and the references cited therein.

It has now surprisingly been found that certain α-amino alkenes which comprise a structural unit of the formula (I)

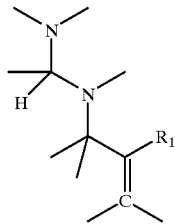

release an amidine group on exposure to visible or UV light. This amidine group is sufficiently basic to initiate a large number of base-catalysable reactions, especially polymerization reactions. The compounds are of high sensitivity and through the choice of the substituent $R_1$ the absorption spectrum can be varied within a wide range.

The compounds make it possible to prepare so-called one-pot systems with base-catalysable oligomers or monomers having an extremely long storage life. A polymerization reaction, for example, is initiated only after exposure to light. The systems can be formulated with little or no solvent, since the compounds can be dissolved in the monomers or oligomers without being affected. The active catalyst is formed only after exposure to light. These systems with base-catalysable oligomers or monomers can be employed for numerous purposes, such as for finishes, coatings, moulding compounds or photolithographic reproductions.

The invention therefore provides organic compounds having a molecular weight of less than 1000, comprising at least one structural unit of the formula (I)

in which $R_1$ is an aromatic or heteroaromatic radical capable of absorbing light in the wavelength range from 200 to 650 nm and in doing so brings about cleavage of the adjacent carbon-nitrogen bond.

By aromatic or heteroaromatic radicals $R_1$ are meant those which conform to the Hückel 4n+2 rule.

The absorption maximum can be varied within a wide range through the choice of the aromatic or heteroaromatic radical $R_1$, and so the photosensitivity of the compounds can be shifted from the UV into the daylight region.

Preference is given to organic compounds in which the structural unit of the formula (I) comprises compounds of the formula (II)

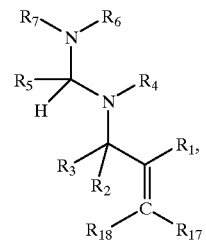

in which $R_1$ is an aromatic or heteroaromatic radical which is capable of absorbing light in the wavelength range from 200 to 650 nm and in doing so brings about cleavage of the adjacent carbon-nitrogen bond;

$R_2$ and $R_3$ independently of one another are hydrogen, $C_1$–$C_{18}$alkyl, $C_3$–$C_{18}$alkenyl, $C_3$–$C_{18}$alkynyl or phenyl and, if $R_2$ is hydrogen or $C_1$–$C_{18}$alkyl, $R_3$ is additionally a group —CO—$R_{14}$ in which $R_{14}$ is $C_1$–$C_{18}$alkyl or phenyl;

$R_5$ is $C_1$–$C_{18}$alkyl or $NR_{15}R_{16}$;

$R_4$, $R_6$, $R_7$, $R_{15}$ and $R_{16}$ independently of one another are hydrogen or $C_1$–$C_{18}$alkyl; or $R_4$ and $R_6$ together form a $C_2$–$C_{12}$alkylene bridge or $R_5$ and $R_7$, independently of $R_4$ and $R_6$, together form a $C_2$–$C_{12}$alkylene bridge or, if $R_5$ is $NR_{15}R_{16}$, $R_{16}$ and $R_7$ together form a $C_2$–$C_{12}$alkylene bridge;

$R_{17}$ is hydrogen or $C_1$–$C_{18}$alkyl;

$R_{18}$ is hydrogen, $C_1$–$C_{18}$alkyl or phenyl substituted by $C_1$–$C_{18}$alkyl, vinyl, $C_3$–$C_{18}$alkenyl, $C_3$–$C_{18}$alkynyl, $C_1$–$C_{18}$haloalkyl, phenyl, $NO_2$, OH, CN, $OR_{10}$, $SR_{10}$, $C(O)R_{11}$, $C(O)OR_{12}$ or halogen; and $R_{10}$, $R_{11}$ and $R_{12}$ are hydrogen or $C_1$–$C_{18}$alkyl.

Alkyl in the various radicals having up to 18 carbon atoms is a branched or unbranched radical such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethyl-hexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Preference is given to alkyl having 1 to 12, especially 1 to 6 carbon atoms.

Alkenyl having 3 to 18 carbon atoms is a branched or unbranched radical such as propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. Preference is given to alkenyl having 3 to 12, especially 3 to 6 carbon atoms.

Alkynyl having 3 to 18 carbon atoms is a branched or unbranched radical such as propynyl

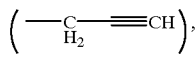

2-butynyl, 3-butynyl, n-2-octynyl, or n-2-octadecynyl. Preference is given to alkynyl having 3 to 12, especially 3 to 6 carbon atoms.

Examples of $C_2$–$C_{12}$alkylene bridges are ethylene, propylene, butylene, pentylene, hexylene, heptylene, octylene, nonylene, decylene, undecylene or dodecylene.

Preference is given to those compounds of the formula II in which
$R^1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphto[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or substituted one or more times by $C_1$–$C_{18}$alkyl, $C_3$–$C_{18}$alkenyl, $C_3$–$C_{18}$alkynyl, $C_1$–$C_{18}$haloalkyl, $NO_2$, $NR_8R_9$, $N_3$, OH, CN, $OR_1$, $SR_{10}$, $C(O)R_{11}$, $C(O)OR_{12}$ or halogen, or $R_1$ is a radical of the formulae A or B

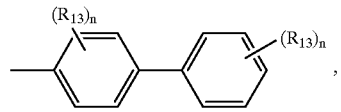

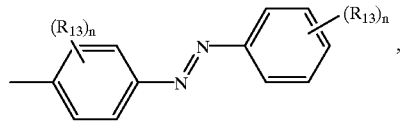

$R_8$, $R_9$, $R_{10}$, $R_{11}$ and $R_{12}$ are hydrogen or $C_1$–$C_{18}$alkyl;
$R_{13}$ is $C_1$–$C_{18}$alkyl, $C_2$–$C_{18}$alkenyl, $C_2$–$C_{18}$alkynyl, $C_1$–$C_{18}$haloalkyl, $NO_2$, $NR_8R_9$, OH, CN, $OR_{10}$, $SR_{10}$, C(O)R, $C(O)OR_{12}$ or halogen; and
n is 0 or a number 1, 2 or 3. Examples of $C_1$–$C_{18}$alkyl, $C_3$–$C_{18}$alkenyl and $C_3$–$C_{18}$alkynyl have already been indicated above.

Halogen is fluorine, chlorine, bromine or iodine.

Examples of $C_1$–$C_{18}$haloalkyl are fully or partly halogenated $C_1$–$C_{18}$alkyl. The halogen (halo) here is F, Cl, Br, or I. Examples are the positional isomers of mono- to decafluoropentyl, mono- to octafluorobutyl, mono- to hexafluoropropyl, mono- to tetrafluoroethyl and mono- and difluoromethyl and also the corresponding chloro, bromo and iodo compounds. Preference is given to the perfluorinated alkyl radicals. Examples of these are perfluoropentyl, perfluorobutyl, perfluoropropyl, perfluoroethyl and, in particular, trifluoromethyl.

Examples of the $NR_8R_9$ amino group are the respective monoalkyl or dialkylamino groups such as methylamino, ethylamino, propylamino, butylamino, pentylamino, hexylamino, octadecylamino, dimethylamino, diethylamino, dipropylamino, diisopropylamino, di-n-butylamino, di-isobutylamino, dipentylamino, dihexylamino or dioctadecylamino. Further dialkylamino groups are those in which the two radicals independently of one another are branched or unbranched, for example methylethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, isopropyl-n-butylamino or isopropylisobutylamino.

The alkoxy group $OR_{10}$ having up to 18 carbon atoms is a branched or unbranched radical such as methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 1 to 12, especially 1 to 8, for example 1 to 6 carbon atoms.

Examples of the thioalkyl group $SR_{10}$ are thiomethyl, thioethyl, thiopropyl, thiobutyl, thiopentyl, thiohexyl, thioheptyl, thiooctyl or thiooctadecyl, it being possible for the alkyl radicals to be linear or branched.

Examples of the radical $R_1$ are phenyl, naphthyl, phenanthryl, anthracyl, biphenylyl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thiathrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, stilbenyl, terphenyl, fluorenyl, phenoxazinyl, methoxyphenyl, 2,4-dimethoxyphenyl, 2,4,6-trimethoxyphenyl, 3,4,5-trimethoxyphenyl, bromophenyl, tolyl, xylyl, mesityl, nitrophenyl, dimethylaminophenyl, diethylaminophenyl, aminophenyl, diaminophenyl, thiomethylphenyl, 1-naphthyl, 2-naphthyl, 1-phenylamino-4-naphthyl, 1-methylnaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7-naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, 1-anthryl, 2-anthryl, 9-anthryl, 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl or 10-methyl-2-phenoxazinyl.

With particular preference $R_1$ is phenyl, naphthyl, pyrenyl, thioxanthyl, thianthrenyl or phenothiazinyl, these radicals being unsubstituted or substituted one or more times by $C_1-C_{18}$alkyl, $C_1-C_{18}$haloalkyl, $NR_8R_9$, CN, $NO_2$, $N_3$, $SR_{10}$ or $OR_{10}$, or $R_1$ is a radical of the abovementioned formulae A or B.

Further particularly preferred compounds are those in which $R_1$ is phenyl, pyrenyl or naphthyl, the radicals phenyl, pyrenyl and naphthyl being unsubstituted or substituted one or more times by CN, $NR_8R_9$, $NO_2$, $CF_3$, $SR_{10}$ or $OR_{10}$, or $R_1$ is a radical of the formulae A or B as defined above.

With very particular preference, $R_1$ is phenyl, 4-aminophenyl, 4-methylthiophenyl, 4-trifluoromethylphenyl, 4-nitrophenyl, 2,4,6-trimethoxyphenyl, 2,4-dimethoxyphenyl, naphthyl, anthracyl, pyrenyl or a radical of the formula A or B as defined above.

$R_2$ and $R_3$ independently of one another are preferably hydrogen or $C_1-C_6$alkyl. It is likewise preferred for $R_4$ and $R_6$ together to be a $C_2-C_6$alkylene bridge.

Preferably, $R_5$ and $R_7$ are a $C_2-C_6$alkylene bridge or, if $R_5$ is $NR_{15}R_{16}$, $R_{16}$ and $R_7$ together are a $C_2-C_6$alkylene bridge.

Preferably, $R_{17}$ is hydrogen or $C_1-C_4$alkyl and $R_{18}$ is hydrogen, $C_1-C_4$alkyl or phenyl.

A particularly preferred group of compounds of the formula (II) are those in which $R_1$ is phenyl, naphthyl or pyrenyl, these radicals being unsubstituted or being substituted one or more times by CN, $NR_8R_9$, $NO_2$, $CF_3$, $SR_{10}$ or $OR_{10}$, or $R_1$ is a radical of the formulae A or B as described above;

n is 0 and the radicals $R_8$, $R_9$, $R_{10}$ and $R_{13}$ are hydrogen or $C_1-C_6$alkyl;

$R_2$ and $R_3$ are hydrogen or $C_1-C_6$alkyl;

$R_4$, $R_6$ and $R_7$ independently of one another are hydrogen or $C_1-C_6$alkyl;

$R_5$ is $C_1-C_6$alkyl or $NR_{15}R_{16}$, where $R_{15}$ and $R_{16}$ are hydrogen or $C_1-C_6$alkyl; or $R_4$ and $R_6$ together form a $C_2-C_6$alkylene bridge; or, independently of $R_4$ and $R_6$, $R_5$ and $R_7$ together form a $C_2-C_6$alkylene bridge or, if $R_5$ is $NR_{15}R_{16}$, $R_{16}$ and $R_7$ together form a $C_2-C_6$alkylene bridge;

$R_{17}$ is hydrogen or $C_1-C_4$alkyl; and $R_{18}$ is hydrogen, $C_1-C_4$alkyl or phenyl.

Particular preference is given to organic compounds of the formula (II) in which $R_1$ is phenyl or naphthyl, the radicals phenyl and naphthyl being unsubstituted or being substituted one or more times by CN, $NR_8R_9$, $NO_2$, $CF_3$, $SR_{10}$ or $OR_{10}$, or $R_1$ is thianthrenyl, fluorenyl or thioxanthyl, or $R_1$ is a radical of the formula A

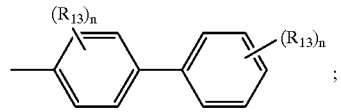

(A)

n is 0 and the radicals $R_8$, $R_9$ and $R_{10}$ are hydrogen or $C_1-C_6$alkyl;

$R_2$ and $R_3$ are hydrogen or $C_1-C_6$alkyl;

$R_4$ and $R_6$ together form a $C_2-C_6$alkylene bridge;

$R_5$ and $R_7$ together form a $C_2-C_6$alkylene bridge;

$R_{17}$ is hydrogen; and $R_{18}$ is hydrogen or $C_1-C_4$alkyl.

The invention additionally provides a process for preparing compounds having the structural unit of the formula (I) as described above, which comprises, in a first step, reacting a compound comprising a structural unit of the formula (III)

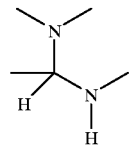

(III)

with a compound comprising a structural unit of the formula IV

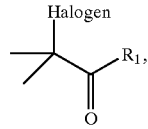

(IV)

in which

Halogen is F, Cl, Br or I and $R_1$ is as defined in claim 1, and, in a second step, carrying out a Wittig reaction, using a phosphonium salt, with the reaction product thus obtained. Preference is given to a process for preparing compounds of the formula (II) which comprises reacting a compound of the formula (V)

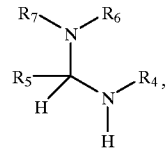

(V)

in which the radicals $R_4$, $R_5$, $R_6$ and $R_7$ are as defined above, including the preferred meanings, with a compound of the formula (VI)

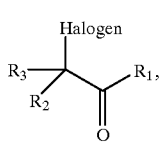

(VI)

in which
the radicals $R_1$, $R_2$ and $R_3$ are as defined above, including the preferred meanings, and Halogen is F, Cl, Br or I,
and, in a second step, conducting a Wittig reaction with the reaction product thus obtained, using a phosphonium salt of the formula VII

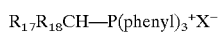

(VII)

in which
$R_{17}$ and $R_{18}$ are as defined above, including the preferred meanings, and X is F, Cl, Br, I or tetrafluoroborate.

Suitable Wittig reagents (phosphonium salts) are obtainable commercially and are mentioned, for example, in Lancaster Chemical Catalogue, Appendix 1, pages A2–A6. Examples are: methyltriphenylphosphonium bromide, methyltriphenylphosphonium iodide, ethyltriphenylphosphonium chloride, ethyltriphenylphosphonium bromide, ethyltriphenylphosphonium iodide, n-propyltriphenylphosphonium bromide, n-butyltriphenylphosphonium chloride, n-butyltriphenylphosphonium bromide, isobutyltriphenylphosphonium bromide, n-amyltriphenylphosphonium bromide, isoamyltriphenylphosphonium bromide, n-hexyltriphenylphosphonium bromide, n-heptyltriphenylphosphonium bromide, n-octyltriphenylphosphonium bromide, n-nonyltriphenylphosphonium bromide, n-decyltriphenylphosphonium bromide, n-undecyltriphenylphosphonium bromide, n-dodecyltriphenylphosphonium bromide, n-tetradecyltriphenylphosphonium bromide, n-hexadecyltriphenylphosphonium bromide, trimethylsilylmethyltriphenylphosphonium iodide, 2-dimethylaminoethyltriphenylphosphonium bromide, 2-chloroethyltriphenylphosphonium bromide, 2-hydroxyethyltriphenylphosphonium bromide, 3-bromopropyltriphenylphosphonium bromide, 4-bromobutyltriphenylphosphonium bromide, 2-(1,3-dioxan-2-yl)ethyltriphenylphosphonium bromide, cyclopropylmethyltriphenylphosphonium bromide, 4-carboxybutyltriphenylphosphonium bromide, 4-carboethoxybutyltriphenylphosphonium bromide, 4-pentenyltriphenylphosphonium bromide, 5-hexenyltriphenylphosphonium bromide, 3-phenylpropyltriphenylphosphonium bromide, ethylenebis(triphenylphosphonium bromide), trimethylenebis(triphenylphosphonium bromide), tetramethylenebis(triphenylphosphonium bromide), pentamethylenebis(triphenylphosphonium bromide), isopropyltriphenylphosphonium iodide, 2-butyltriphenylphosphonium bromide, 2-amyltriphenylphosphonium bromide, cyclopropyltriphenylphosphonium bromide, cyclopentyltriphenylphosphonium bromide, cyclohexyltriphenylphosphonium bromide, cycloheptyltriphenylphosphonium bromide, allyltiphenylphosphonium chloride, allyltriphenylphosphonium bromide, 2-methylallyltriphenylphosphonium chloride, 3-methylailyltriphenylphosphonium chloride, 3,3-dimethylallyltriphenylphosphonium bromide, 2-butene-1,4-bis(triphenylphosphonium chloride), cinnamyltriphenylphosphonium chloride, cinnamyltriphenylphosphonium bromide, propargyltriphenylphosphonium bromide, benzyltriphenylphosphonium chloride, benzyltriphenylphosphonium bromide, benzyltriphenylphosphonium iodide, 2-methylbenzyltriphenylphosphonium chloride, 2-methylbenzyltriphenylphosphonium bromide, 3-methylbenzyltriphenylphosphonium chloride, 4-methylbenzyltriphenylphosphonium chloride, 4-methylbenzyltriphenylphosphonium bromide, 2-hydroxybenzyltriphenylphosphonium bromide, 4-methoxybenzyltriphenylphosphonium chloride, 4-ethoxybenzyltriphenylphosphonium bromide, 4-butoxybenzyltriphenylphosphonium bromide, 4-fluorobenzyltriphenylphosphonium chloride, 4-chlorobenzyltriphenylphosphonium chloride, 4-bromobenzyltriphenylphosphonium bromide, 4-cyanobenzyltriphenylphosphonium chloride, 4-carbomethoxybenzyltriphenylphosphonium bromide, 2-nitrobenzyltriphenylphosphonium bromide hydrate, 4-nitrobenzyltriphenylphosphonium bromide, o-xylylenebis(triphenylphosphonium bromide), p-xylylenebis(triphenylphosphonium chloride), p-xylylenebis(triphenylphosphonium bromide), 1-naphthylmethyltriphenylphosphonium chloride, benzhydryltriphenylphosphonium chloride, hydroxymethyltriphenylphosphonium chloride, methoxymethyltriphenylphosphonium chloride, chloromethyltriphenylphosphonium iodide, methylthiomethyltriphenylphosphonium chloride, phenylthiomethyltriphenylphosphonium chloride, 1,3-dithian-2-yltriphenylphosphonium chloride, formylmethyltriphenylphosphonium chloride, acetonyltriphenylphosphonium chloride, acetonyltriphenylphosphonium bromide, phenacyltriphenylphosphonium bromide, methylphenacyltriphenylphosphonium bromide, carbomethoxymethyltriphenylphosphonium chloride, carbomethoxymethyltriphenylphosphonium bromide, carboethoxymethyltriphenylphosphonium chloride, carboethoxymethyltriphenylphosphonium bromide, 1-carboethoxyethyltriphenylphosphonium bromide, methyl 4-(triphenylphosphonio)crotonate bromide, 1-carboethoxycyclopropyltriphenylphosphonium tetrafluoroborate, cyanomethyltriphenylphosphonium chloride, 2-(triphenylphosphoranylidene)succinic anhydride, 9-fluorenyltriphenylphosphonium bromide, vinyltriphenylphosphonium bromide, or 1,2-vinylenebis(triphenylphosphonium bromide).

The reaction of compounds having formula (V) with compounds having formula (VI) can be conducted in a manner known per se. Advantageously, a solvent or mixture of solvents is used, examples-being hydrocarbons such as benzene, toluene, xylene, etc., halogenated hydrocarbons such as methylene chloride, chloroform, carbon tetrachloride, chlorobenzene, etc., alkanols such as methanol, ethanol, ethylene glycol monomethyl ether, etc., and ethers such as diethyl ether, dibutyl ether, ethylene glycol dimethyl ether, etc., and mixtures of such solvents.

The reaction can judiciously be conducted within a temperature range from −10° C. to 100° C. Preference is given to reaction temperatures from 10° C. to 50° C.

The Wittig reaction can be carried out in a conventional manner. It is advantageous to use a solvent or solvent mixture, e.g. hydrocarbons such as benzene, toluene, xylene, etc., halogenated hydrocarbons such as methylene chloride, chloroform, carbon tetrachloride, chlorobenzene, etc., alkanols such as methanol, ethanol, ethylene glycol monomethyl ether, etc. and ethers such as diethyl ether, dibutyl ether, ethylene glycol dimethyl ether, etc. and mixtures of these solvents.

The reaction can be carried out within a temperature range from −10° C. to 100° C. Ranges are preferably from 10° C. to 70° C.

In the course of the preparation of the photolatent bases of the invention it is possible for isomer mixtures to be formed. These can be separated by customary methods familiar to the skilled worker. Alternatively, it is possible to employ the particular resulting isomer mixtures directly as photolatent bases.

The invention furthermore provides a process for preparing a compound of the formula (VII)

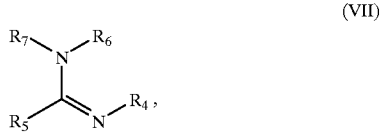

(VII)

in which
$R_4$, $R_5$, $R_6$ and $R_7$ are as defined above, including their preferred meanings, which comprises exposing a compound of the formula (II)

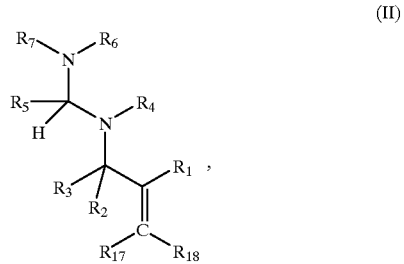

(II)

in which
the radicals $R_1$, $R_2$, $R_3$, $R_4$, $R_5$, $R_6$, $R_7$, $R_{17}$ and $R_{18}$ are as defined above, including their preferred meanings,
to light having a wavelength from 200 nm to 650 nm. The reaction is advantageously carried out in a solvent or solvent mixture. The concentration of the compounds of the formula (II) is advantageously adjusted so that virtually all of the light is absorbed in the reaction vessel.

The reaction solution is preferably stirred and, if desired, cooled in the course of the exposure.

Suitable solvents are those listed above.

In accordance with the invention, the organic compounds comprising a structural unit of formula I can be used as photolatent bases.

The invention therefore additionally provides a composition comprising
A) at least one compound having a structural unit of the formula (I) and
B) at least one organic compound capable of a base-catalysed addition or substitution reaction.

Preference is given to the organic compounds of the formula (II) described above.

The base-catalysed addition or substitution reaction can be carried out with low molecular mass compounds (monomers), with oligomers, with polymeric compounds or with a mixture of these compounds. Examples of reactions which can be carried out both with monomers and with oligomers/polymers using the novel photoinitiators are the Knoevenagel reaction or the Michael addition reaction.

Of particular importance are compositions in which component B) is an anionically polymerizable or crosslinkable organic material.

The organic material can be in the form of mono- or polyfunctional monomers, oligomers or polymers.

Particularly preferred oligomeric/polymeric systems are binders as are customary in the coatings industry.

Examples of such base-catalysable binders are:
a) Acrylate copolymers having alkoxysilane or alkoxysiloxane side groups, for example the polymers described in U.S. Pat. No. 4,772,672 or U.S. Pat. No. 4,444,974;
b) Two-component systems comprising hydroxyl-containing polyacrylates, polyesters and/or polyethers and aliphatic or aromatic polyisocyanates;
c) Two-component systems comprising functional polyacrylates and a polyepoxide, where the polyacrylate contains carboxyl and anhydride groups;
d) Two-component systems comprising fluorine-modified or silicone-modified hydroxyl-containing polyacrylates, polyesters and/or polyethers and aliphatic or aromatic polyisocyanates;
e) Two-component systems comprising (poly)ketimines and aliphatic or aromatic polyisocyanates;
f) Two-component systems comprising (poly)ketimines and unsaturated acrylate resins or acetoacetate resins or methyl α-acrylamidomethylglycolate;
h) Two-component systems comprising (poly)oxazolidines and polyacrylates containing anhydride groups, or unsaturated acrylate resins or polyisocyanates,
i) Two-component systems comprising epoxy-functional polyacrylates and carboxyl-containing or amino-containing polyacrylates;
l) Polymers based on allyl glycidyl ether;
m) Two-component systems comprising a (poly)alcohol and a (poly)isocyanate;
n) Two-component systems comprising an α,β-ethylenically unsaturated carbonyl compound and a polymer which contains activated $CH_2$ groups, it being possible for the activated $CH_2$ groups to be present either in the main chain or in the side chain or in both, as is described, for example, in EP-B-0 161 697 for (poly)malonate groups. Other compounds having activated $CH_2$ groups are (poly)acetoacetates and (poly)cyanoacetates.

Among these base-catalysable binders particular preference is given to the following:
b) Two-component systems comprising hydroxyl-containing polyacrylates, polyesters and/or polyethers and aliphatic or aromatic polyisocyanates;
c) Two-component systems comprising functional polyacrylates and a polyepoxide, the polyacrylate containing carboxyl, anhydride groups;
i) Two component systems comprising epoxy-functional polyacrylates and carboxyl-containing or amino-containing polyacrylates;
m) Two-component systems comprising a (poly)alcohol and a (poly)isocyanate, and
n) Two-component systems comprising an apethylenically unsaturated carbonyl compound and a polymer which contains activated $CH_2$ groups, it being possible for the activated $CH_2$ groups to be present either in the main chain or in the side chain or in both.

Two-component systems comprising an α,β-ethylenically unsaturated carbonyl compound and a (poly)malonate, and their preparation, are described in EP-B-0 161 687. The malonate group here can be attached in a polyurethane, polyester, polyacrylate, epoxy resin, polyamide or polyvinyl polymer either in the main chain or in a side chain. The α,β-ethyl-enically unsaturated carbonyl compound employed can be any double bond activated by a carbonyl group. Examples are esters or amides of acrylic acid or methacrylic acid. In the ester groups it is also possible for additional hydroxyl groups to be present. Diesters and triesters are also possible.

Typical examples are hexanediol diacrylate or trimethylolpropane triacrylate. Instead of the acrylic acid it is also possible to use other acids and their esters or amides, such as crotonic or cinnamic acid.

Under base catalysis, the components of the system react with one another at room temperature to form a crosslinked coating system which is suitable for numerous applications. Owing to its good inherent weathering resistance it is suitable, for example, for exterior applications as well and can, if required, be additionally stabilized by UV absorbers and other light stabilizers.

Other systems suitable as component B) in the novel compositions are epoxy systems. Epoxy resins are suitable for preparing novel, curable mixtures comprising epoxy resins as component B) are those which are customary in epoxy resin technology, examples of such epoxy resins being:

I) Polyglycidyl and poly(β-methylglycidyl) esters, obtainable by reacting a compound, having at least two carboxyl groups in the molecule with epichlorohydrin or β-methylepichlorohydrin. The reaction is judiciously carried out in the presence of bases. As the compound having at least two carboxyl groups in the molecule it is possible to use aliphatic polycarboxylic acids. Examples of such polycarboxylic acids are oxalic, succinic, glutaric, adipic, pimelic, suberic, azelaic or dimerized or trimerized linoleic acid. It is also possible, however, to employ cycloaliphatic polycarboxylic acids, such as tetrahydrophthalic, 4-methyltetrahydrophthalic, hexahydrophthalic or 4-methylhexahydrophthalic acid, for example. Aromatic polycarboxylic acids, furthermore, can be used, such as phthalic, isophthalic or terephthalic acid, for example.

II) Polyglycidyl or poly(β-methylglycidyl) ethers, obtainable by reacting a compound having at least two free alcoholic hydroxyl groups and/or phenolic hydroxyl groups with epichlorohydrin or ,-methylepichlorohydrin under alkaline conditions or in the presence of an acidic catalyst with subsequent alkali treatment.

The glycidyl ethers of this type are derived, for example, from acyclic alcohols, such as ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol, sorbitol, and from polyepichlorohydrins. They also derive, however, for example, from cycloaliphatic alcohols, such as 1,4-cyclohexanedimethanol, bis(4-hydroxycyclohexyl)methane or 2,2-bis(4-hydroxycyclohexyl)propane, or possess aromatic nuclei, such as N,N-bis(2-hydroxyethyl)aniline or p,p'-bis(2-hydroxyethylamino)-diphenylmethane. The glycidyl ethers can also be derived from mononuclear phenols, such as resorcinol or hydroquinone, for example, or are based on polynuclear phenols, such as bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl)propane, 2,2-bis(3,5-dibromo-4-hydroxyphenyl)propane and from novolaks, obtainable by condensing aldehydes, such as formaldehyde, acetaldehyde, chloral or furfuraldehyde, with phenols, such as phenol, or with phenols whose nucleus is substituted by chlorine atoms or $C_1$–$C_9$alkyl groups, examples being 4-chlorophenol, 2-methylphenol, or 4-tert-butylphenol, or by condensation with bisphenols, those of the type specified above.

III) Poly(N-glycidyl) compounds, obtainable by dehydrochlorination of the reaction products of epichlorohydrin with amines containing at least two amine hydrogen atoms. These amines are, for example, aniline, n-butylamine, bis(4-aminophenyl)methane, m-xylylenediamine or bis(4-methylaminophenyl)methane.

The poly(N-glycidyl) compounds also, however, include triglycidyl isocyanurate, N,N'-digiycidyl derivatives of cycloalkyleneureas, such as ethyleneurea or 1,3-propyleneurea, and diglycidyl derivatives of hydantoins, such as of 5,5-dimethylhydantoin.

IV) Poly(S-glycidyl) compounds, for example di-S-glycidyl derivatives derived from dithiols such as ethane-1,2-dithiol or bis(4-mercaptomethylphenyl) ether.

V) Cycloaliphatic epoxy resins, for example bis(2,3-epoxycyclopentyl) ether, 2,3-epoxy-cyclopentyl glycidyl ether, 1,2-bis(2,3-epoxycyclopentyloxy)ethane or 3,4-epoxycyclohexyl-methyl 3',4'-epoxycyclohexanecarboxylate.

Alternatively it is possible to use epoxy resins in which the 1,2-epoxide groups are attached to different heteroatoms and/or functional groups; these compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Mixtures of epoxy resins can also be used as component B).

Also in accordance with the invention, therefore, are compositions comprising as component B) an epoxy resin or a mixture of different epoxy resins.

The compositions comprise the photoinitiator, component A), preferably in an amount of from 0.01 to 10% by weight, based on the component B).

In addition to the photoinitiator, component A), the photopolymerizable mixtures may include various additives. Examples of these are thermal inhibitors which are intended to prevent premature polymerization, such as hydroquinone, hydroquinone derivatives, p-methoxyphenol, β-naphthol or sterically hindered phenols such as 2,6-di(tert-butyl)-p-cresol, for example. To increase the dark storage stability it is possible, for example, to use copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, such as N-diethylhydroxylamine. To exclude atmospheric oxygen during polymerization it is possible to add paraffin or similar waxlike substances, which owing to their lack of solubility in the polymer migrate to the surface at the beginning of polymerization where they form a transparent surface layer which prevents the ingress of air. It is likewise possible to apply an oxygen-impermeable layer. Light stabilizers which can be added, in a small amount, are UV absorbers such as those, for example, of the hydroxyphenylbenzotriazole, hydroxyphenyl-benzophenone, oxalamide or hydroxyphenyl-s-triazine type. Individual compounds or mixtures of these compounds can be used, with or without the deployment of sterically hindered amines (HALS).

Examples of such UV absorbers and light stabilizers are given below.

1. 2-(2'-Hvdroxyyhenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxy-phenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis($\alpha,\alpha$-dimethylbenzyl)-2'-hydroxyphenyl)benzo-triazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]benzotriazole with polyethylene glycol 300; [R—$CH_2CH_2$—COO$(CH_2)_3]_2$— where R=3'-tert-butyl-4'-hydroxy-5'-2H-benzotriazol-2-ylphenyl.

2. 2-Hydroxybenzophenones, for example the 4-hydroxy, 4-methoxy-, 4-octoxy-, 4-decyloxy, 4-dodecyloxy, 4-benzyloxy, 4,2',4'-trihydroxy and 2'-hydroxy-4,4'-dimethoxy derivative.

3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxy-benzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

4. Acrvlates, for example ethyl or isooctyl $\alpha$-cyano-$\beta,\beta$-diphenylacrylate, methyl $\alpha$-carbo-methoxycinnamate, methyl and butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methyl-indoline.

5. Sterically hindered amines, such as bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro-([4.5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl) hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis(3-aminopropylamino)ethane, condensation product of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-di-dodecyloxy-5,5'di-tert-butyloxanilide, 2-ethoxy-2'-ethyl-oxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)-phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyloxy-(2-hydroxypropyl)oxy-2-hydroxyphenyl]-4,6-bis(2,4-dimethylphenyl)-1,3,5-triazine.

8. Phosphites and phosphonites, for example, triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bis-isodecyloxy pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyldibenzo[d,g]-1,3,2-dioxaphosphocin, bis-(2,4-di-tert-butyl-6-methylphenyl) methyl phosphite, bis(2,4-di-tert-butyl-6-methylphenyl) ethyl phosphite.

Examples of further additives are:

Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibres of other natural products, synthetic fibres.

Other additives, for example plasticizers, lubricants, emulsifiers, pigments, rheological additives, catalysts, levelling assistants, optical brighteners, flameproofing agents, antistatics, blowing agents.

In addition to the additives indicated above it is also possible for additional coinitiators to be present. In general these are dyes which improve the overall quantum yield by means, for example, of energy transfer or electron transfer. Examples of suitable dyes which can be added as coinitiators are triarylmethanes, for example malachite green, indolines, thiazines, for example methylene blue, xanthones, thioxanthones, oxazines, acridines or phenazines, for example safranine, and rhodamines of the formula

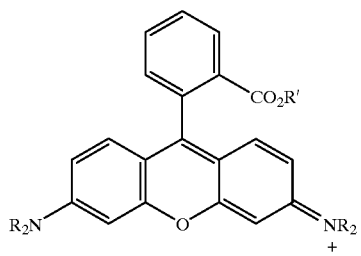

in
which R is alkyl or aryl and R' is hydrogen, an alkyl or aryl radical, for example Rhodamine B, Rhodamine 6G or Violamine R, and also Sulforhodamine B or Sulforhodamine G.

Preference is given to thioxanthones, oxazines, acridines, phenazines and rhodamines.

Likewise suitable in this context are combinations of dyes with borates, as are described, for example, in U.S. Pat. No. 4,772,530, GB 2 307 474, GB 2 307 473, GB 2 307 472 and EP 775 706.

In addition to the above-described base-catalysable (curable) binders, component B), the composition may also include other binders as well. Further olefinically unsaturated compounds, for example, are possible. The unsaturated compounds may include one or more olefinically double bonds. They may be of low molecular mass (monomeric) or higher molecular mass (oligomeric). Examples of monomers having a double bond are alkyl or hydroxyalkyl acrylates or methacrylates, such as methyl, ethyl, butyl, 2-ethylhexyl or 2-hydroxyethyl acrylate, isbornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers having two or more double bonds are the diacrylates of ethylene glycol, propylene glycol, neopentyl glycol, hexamethylene glycol or bisphenol A, 4,4'-bis(2-acryloyloxyethoxy)diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris(2-acryloylethyl)isocyanurate.

Examples of polyunsaturated compounds of relatively high molecular mass (oligomers) are acrylicized epoxy resins, acrylicized polyesters or polyesters containing vinyl ether groups or epoxy groups, polyurethanes and polyethers. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. In particular, combinations of vinyl ether-functional oligomers and polymers as are described in WO 90/01512 are very suitable. Also suitable, however, are copolymers of vinyl ether and maleic acid-functionalized monomers. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

If, in addition, use is made of such free-radically curable monomers, oligomers/polymers then it is judicious to add a further photoinitiator which dissociates into free radicals. Such photoinitiators are known and are produced industrially. Examples are benzophenone, benzophenone derivatives, acetophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacyl phosphine oxides, bisacylphosphine oxides, ferrocenes or titanocenes.

Examples are specified in EP-A-284 561. Polymer systems of this kind, in which curing/crosslinking takes place by different mechanisms, are also referred to as hybrid systems.

The novel compositions can also have added to them non-reactive binders, which is particularly judicious if the photopolymerizable compounds are liquid or viscous substances. The amount of the non-reactive binder can be, for example, 5–95%, preferably 10–90% and, in particular, 40–90% by weight, based on the overall solids content. The choice of non-reactive binder is made in accordance with the field of use and with the properties required for this use, such as the possibility for development in aqueous and organic solvent systems, adhesion to substrates, and sensitivity to oxygen.

Examples of suitable binders are polymers having a molecular weight of around 5000–2,000,000, preferably 10,000–1,000,000. Examples are: homo- and copolymeric acrylates and methacrylates, for example copolymers of methyl methacrylate/ethyl acrylate/methacrylic acid, poly (alkyl methacrylates), poly(alkyl acrylates); cellulose esters and ethers, such as cellulose acetate, cellulose acetate butyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide) and polyesters such as poly(ethylene glycol terephtalate) and poly(hexamethylene glycol succinate).

The invention additionally provides a method of implementing base-catalysed reactions which comprises subjecting
A) A) at least one compound having a structural unit of the formula (I)

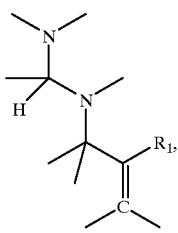

in which

R₁ is an aromatic or heteroaromatic radical which is capable of absorbing light in the wavelength range from 200 to 650 nm and in doing so brings about cleavage of the adjacent carbon-nitrogen bond;

and B) at least one organic compound which is capable of a base-catalysed reaction, that is a composition as described above, to irradiation with light having a wavelength of from 200 nm to 650 nm.

Component A) is preferably an organic compound as described above of the formula (II), including the preferred meanings indicated.

Examples and preferred meanings for base-catalysed reactions have already been given above.

In some cases it may be advantageous to carry out heating during or after exposure to light. In this way it is possible in many cases to accelerate the crosslinking reaction.

Furthermore the method described above for producing coatings, moulding compositions or photostructured layers is according to the invention.

The sensitivity of the novel compositions to light generally extends from about 200 nm through the UV region and into the infrared region (about 20,000 nm, in particular 1200 nm) and therefore spans a very broad range. Suitable radiation comprises, for example, sunlight or light from artificial light sources. Therefore, a large number of very different types of light source can be used. Both point sources and flat radiators (lamp carpets) are suitable. Examples are carbon arc lamps, xenon arc lamps, medium-pressure, high-pressure and low-pressure mercury lamps, doped if desired with metal halides (metal halogen lamps), microwave-stimulated metal vapour lamps, excimer lamps, superactinic fluorescent tubes, fluorescent lamps, incandescent argon lamps, electronic flashlights, photographic flood lamps, electron beams and X-rays, produced by means of synchrotrons or laser plasma. The distance between the lamp and the substrate according to the invention which is to be exposed can vary depending on the application and on the type and/or power of the lamp, for example between 2 cm and 150 cm. Also especially suitable are laser light sources, for example excimer lasers. Lasers in the visible region or in the IR region can also be employed. Very advantageous here is the high sensitivity of the novel materials and the possibility of adapting a dye as coinitiator to the laser line. By this method it is possible to produce printed circuits in the electronics industry, lithographic offset printing plates or relief printing plates, and also photographic image recording materials.

The novel compositions can be employed for various purposes, for example as printing inks, as clearcoats, as white paints, for example for wood or metal, as coating materials, inter alia for paper, wood, metal or plastic, as powder coatings, as daylight-curable coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, including pressure-sensitive adhesives, as laminating resins, as etch resists or permanent resists and as solder masks for electronic circuits, for the production of three-dimensional articles by mass curing (UV curing in transparent moulds) or by the stereolithography process, as is described, for example, in U.S. Pat. No. 4,575,330, for the preparation of composite materials (for example styrenic polyesters, which may contain glass fibres and/or other fibres and other assistants) and other thick-layer compositions, for the coating or encapsulation of electronic components, or as coatings for optical fibres.

In surface coatings, it is common to use mixtures of a prepolymer with polyunsaturated monomers which also contain a monounsaturated monomer. The prepolymer here is primarily responsible for the properties of the coating film, and varying it allows the skilled worker to influence the properties of the cured film. The polyunsaturated monomer functions as a crosslinker, which renders the coating film insoluble. The monounsaturated monomer functions as a reactive diluent, by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleinimides, polychalcones or polyimides, as described in DE-A-2 308 830.

The novel photocurable compositions are suitable, for example, as coating materials for substrates of all kinds, examples being wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is the intention to apply a protective coating or, by imagewise exposure, an image.

The substrates can be coated by applying a liquid composition, a solution or suspension to the substrate. The choice of solvent and the concentration depend predominantly on the type of composition and the coating process. The solvent should be inert: in other words, it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the solution is applied uniformly to a substrate, for example by spin coating, dip coating, knife coating, curtain coating, brushing, spraying—especially electrostatic spraying—and reverse roll coating and by electrophoretic deposition. It is also possible to apply the photosensitive layer to a temporary, flexible support and then to coat the final substrate, for example a copper-clad circuit board, by means of layer transfer via lamination.

The amount applied (layer thickness) and the nature of the substrate (layer support) are functions of the desired field of application. The range of layer thicknesses generally comprises values from about 0.1 μm to more than 100 μm.

The novel radiation-sensitive compositions can also be subjected to imagewise exposure. In this case they are used as negative resists. They are suitable for electronics (galvanoresists, etch resists and solder resists), for the production of printing plates, such as offset printing plates, flexographic and relief printing plates or screen printing plates, for the production of marking stamps, and can be used for chemical milling or as micro resists in the production of integrated circuits. There is a correspondingly wide range of variation in the possible layer supports and in the processing conditions of the coated substrates.

The term "imagewise" exposure relates both to exposure through a photomask containing a predetermined pattern, for example a slide, exposure by a laser beam which is moved under computer control, for example, over the surface of the coated substrate and so generates an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50–150° C. and preferably 80–130° C.; the duration of the thermal treatment is generally between 0.25 and 10 minutes.

A further field of use for photocuring is that of metal coating, for example the surface-coating of metal panels and tubes, cans or bottle tops, and photocuring on polymer coatings, for example of floor or wall coverings based on PVC.

Examples of the photocuring of paper coatings are the colourless varnishing of labels, record sleeves or book covers.

The use of the novel compounds for curing shaped articles made from composite compositions is likewise of interest. The composite composition is made up of a self-supporting matrix material, for example a glass-fibre fabric, or else, for example, of plant fibres [cf. K.-P. Mieck, T. Reussmann in Kunststoffe 85 (1995), 366–370], which is impregnated with the photocuring formulation. Shaped articles which are produced from composite compositions using the compounds according to the invention are of high mechanical stability and resistance. The compounds of the invention can also be used as photocuring agents in moulding, impregnating and coating compositions, as are described, for example, in EP-A-7086. Examples of such compositions are fine coating resins on which stringent requirements are placed with respect to their curing activity and resistance to yellowing, or fibre-reinforced moldings such as planar or longitudinally or transversely corrugated light diffusing panels.

The invention additionally provides for the use of a compound as described above comprising structural unit of the formula (I), as a photoinitiator for photochemically induced, base-catalysed addition or substitution reactions.

Examples of preferred compounds comprising a structural element of the formula (I), as well as of substrates suitable for base-catalysed addition or substitution reactions have been given above.

The invention provides, furthermore, a coated substrate which has been coated on at least one surface with a composition as described above, and a process for the photographic production of relief images, in which a coated substrate is subjected to imagewise exposure and then the unexposed areas are removed with a solvent. Of particular interest in this context is the abovementioned exposure by means of a laser beam. The invention additionally provides a polymerized or crosslinked composition as described above.

The examples which follow illustrate the invention.

Examples A

Preparing the Photoinitiators
General Preparation Method a) A solution of the corresponding α-bromoketone in toluene is added with stirring to a solution of 1,5-diazabicyclo[4.3.0]nonane in toluene and is stirred further overnight at room temperature. The reaction mixture is filtered, washed with demineralized water and dried over $MgSO_4$. It is subsequently dried further in vacuo to give yields of about 85% of the corresponding α-aminoketone.

b) Methyltriphenylphosphonium bromide and sodium amide are stirred in dichloromethane for 15 minutes, then a solution of the α-amino ketone prepared under a), in dichloromethane, is added and the mixture is stirred at room temperature for 18 hours. The solution is filtered and the filtrate is concentrated in vacuo. The crude yield of the resulting α-amino ketone is 65–85%.

The molar extinction coefficients ε in the examples have the dimension l/mol cm.

Example A1

$R_1$=biphenylyl, $R_2$=$R_3$=H, $R_4$/$R_6$=—$(CH_2)_3$—, $R_5$/$R_7$=—$(CH_2)_3$—,
$R_{17}$=$R_{18}$=H

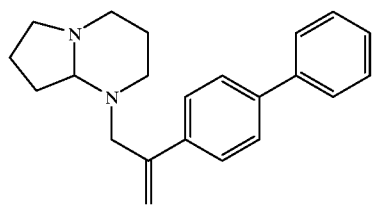

Analysis calculated for $C_{22}H_{26}N_2$: C 82.97; H 8.23; N 8.80. Found: C 82.83; H 8.26; N 8.59. U.V. ($CHCl_3$) max. at 275 nm (ε 21600).

I.R. (KBr) 1625 and 1600 $cm^{-1}$ (C=C).

$^1$H NMR ($CDCl_3$); 7.66–7.28 (9H, m, ArH), 5.51 (1H, s, =CH), 5.29 (1H, s, =CH), 3.83 (1H, d, J 13.3 Hz, $NCH_2C$(CH2)Ph), 3.07 (3H, m, $NCH_2$), 2.89 (1H, d, J 13.3 Hz, $NCH_2C(CH_2)$Ph), 2.38–1.12 (10H, m, CH2).

$^{13}$C NMR ($CDCl_3$): 144.14, 141.02, 140.27, 139.31, 128.82, 127.25, 127.08, 126.99, 126.92, 115.43, 85.08, 58.92, 52.33, 51.92, 51.19, 29.52, 24.75 and 19.55.

m/z (EI) 318 (M+)

Example A2

$R_1$=2-naphthyl, $R_2$=$R_3$=H, $R_4$/$R_6$=—$(CH_2)_3$—, $R_5$/$R_7$=—$(CH_2)_3$—,
$R_{17}$=$R_{18}$=H

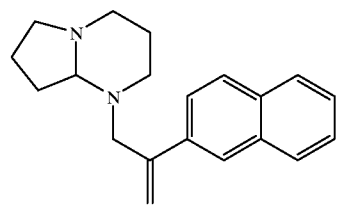

Analysis calculated for $C_{20}H_{24}N_2$: C 82.15; H 8.27; N 9.58. Found: C 82.25; H 8.25; N 9.24. U.V. ($CHCl_3$) max. at 247 nm (ε 35600) and 287 nm (ε 8600).

I.R. (KBr) 1625 and 1595 $cm^{-1}$ (C=C).

$^1$H NMR ($CDCl_3$): 7.95 (1H, s, ArH), 7.85–7.65 (4H, m, ArH), 7.45–7.35 (2H, m, ArH), 5.58 (1H, s, =CH), 5.39 (1H, s, =CH), 3.88 (1H, d, J 13.6 Hz, $NCH_2C(CH_2)$Ph), 3.07 (3H, m, $NCH_2$), 2.97 (1H, d, J 13.7 Hz, $NCH_2C(CH_2)$Ph), 2.44–1.45 (10H, m, $CH_2$).

<sup>13</sup>C NMR (CDCl$_3$): 144.57, 137.84, 133.41, 132.97, 128.37, 127.68, 127.53, 125.96, 125.78, 125.15, 124.94, 115.79, 84.94, 58.65, 52.21, 52.09, 51.12, 29.49, 24.58 and 19.58.

m/z (EI) 292 (M+).

Example A3

$R_1$=4-diethylaminophenyl, $R_2$=$R_3$=H, $R_4/R_6$=—(CH$_2$)$_3$—, $R_5/R_7$=—(CH$_2$)$_3$—,
$R_{17}$=$R_{18}$=H

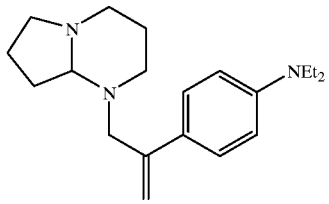

U.V. (CHCl$_3$) max. at 245 nm ($\epsilon$ 3700) and 305 nm ($\epsilon$ 16100). I.R. (KBr) 1610 cm−1 and 1520 cm−1 (C=C).

$^1$H NMR (CDCl$_3$): 7.48 (2H, d, ArH), 6.58 (2H, d, ArH), 5.32 (1H, s, =CH), 5.05 (1H, s, =CH), 3.74 (1H, d, J 13.1 Hz, NCH$_2$C(CH$_2$)Ph), 3.32 (4H, q, J 7.1 Hz, NCH$_2$CH$_3$), 3.06 (3H, M, NCH$_2$), 2.80 (1H, d, J 13.1 Hz, NCH$_2$C(CH$_2$)Ph), 2.36 1.23 (10H, m, CH$_2$) and 1.13 (6H, t, J 7.1 Hz, CH$_3$).

$^{13}$C NMR (CDCl$_3$): 147.21, 143.63, 131.43, 127.36, 111.34, 110.07, 84.21, 59.02, 52.30, 51.81, 51.24, 44.40, 29.42. 24.75, 19.53 and 12.71.

m/z (EI) 313 (M+).

Example A4

$R_1$=4-thiomethylphenyl, $R_2$=$R_3$=H, $R_4/R_6$=—(CH$_2$)$_3$—, $R_5/R_7$=—(CH$_2$)$_3$—.
$R_{17}$=$R_{18}$=H

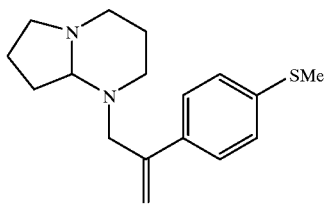

U.V. (CHCl$_3$) max. at 280 nm ($\epsilon$ 13800). I.R. (KBr) 1670, 1625 and 1595 cm$^{-1}$ (C=C).

$^1$H NMR (CDCl$_3$): 7.48 (2H, d, ArH), 7.16 (2H, d, ArH), 5.41 (1H, s, =CH), 5.21 (1H, s, =CH), 3.74 (1H, d, J 13.2 Hz, NCH$_2$C(CH$_2$)Ph), 3.05 (3H, m, NCH$_2$), 2.83 (1H, d, J 13.2 Hz, NCH$_2$C(CH$_2$)Ph), 2.44 (3H, s, SCH$_3$), 2.30–1.4 (10H, m, CH$_2$).

$^{13}$C NMR (CDCl$_3$): 143.83, 137.46, 137.16, 126.89, 126.49, 114.93, 84.99, 58.85, 52.25, 51.78, 51.12, 29.42, 24.67, 19.48 and 15.97.

m/z (EI) 288 (M).

Example A5

$R_1$=phenyl, $R_2$=H, $R_3$=CH$_3$, $R_4/R_6$=—(CH$_2$)$_3$—, $R_5/R_7$=—(CH$_2$)$_3$—,
$R_{17}R_8$=H

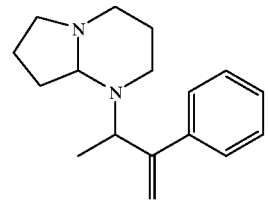

Analysis calculated for C$_{17}$H$_{24}$N$_2$: C 79.64; H 9.43; N 10.93. Found: C 79.64; H 9.46; N 10.75. U.V. (CHCl$_3$) max. at 244 nm ($\epsilon$ 6700).

I.R. (KBr) 1630, 1600 and 1575 cm$^{-1}$ (C=C).

$^1$H NMR (CDCl$_3$): 7.50–7.17 (5H, m, ArH), 5.35 (0.75H, s, =CH), 5.24 (0.25H, s, =CH), 5.15 (0.75H, s, =CH), 5.10 (0.25H, s, =CH), 4.06 (1H, q, J 6.8 Hz, NCHCH$_3$), 2.94 (3H, m, NCH$_2$), 2.63 (1H, m, NCH$_2$), 2.2–1.2 (9H, m, CH$_2$), 1.36 (0.75H, d, J 7.0 Hz, CH$_3$) and 1.13 (2.25H, d, J 6.8 Hz, CH$_3$).

$^{13}$C NMR (CDCl$_3$): 150.38, 142.89, 128.16, 127.04, 126.93, 114.95 (secondary diastereomer), 114.48 (main diastereomer), 82.18 (secondary diastereomer), 82.03 (main diastereomer), 56.37, 52.24, 51.60, 43.27, 28.99 (secondary diastereomer), 28.73 (main diastereomer), 25.62 (main diastereomer), 25.14 (main diastereomer), 19.36 and 9.35.

m/z (DCI) 256 (M+).

Example A6

$R_1$=4-biphenyl, $R_2$=H, $R_3$=CH$_3$, $R_4/R_6$=—(CH$_2$)$_3$—, $R_5/R_7$=—(CH$_2$)$_3$—,
$R_{17}$=$R_{18}$=H.

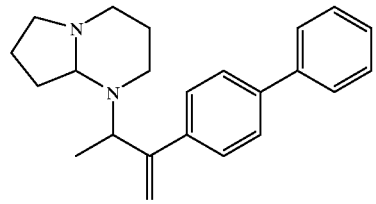

U.V. (CHCl$_3$) max at 266 nm ($\epsilon$ 19200).

I.R. (KBr) 1625, 1600, 1580 cm$^{-1}$ (C=C).

$^1$H NMR (CDCl$_3$): 7.49–7.14 (9h, m ArH), 5.29 (0.8H, s, =CH), 5.18 (0.2H, s, =CH), 5.05 (0.8H, s =CH), 5.00 (0.2H, s =CH), 4.00 (1H, q, J 6.5 Hz, NCHCH$_3$), 2.91 (2H, m, NCH$_2$), 2.75 (1H, m, NCH$_2$), 2.52 (1H, m, NCH), 2.1–1.2 (9H, m, CH$_2$) and 1.04 (3H, d, J 6.8 HzM CH$_3$).

$^{13}$C NMR (CDCl$_3$): 150.00, 141.80, 141.18, 139.88, 128.83, 128.74, 127.46, 127.33, 127.11, 127.02, 126.90, 126.85, 114.51, 82.18, 57.33 (secondary diastereomer), 56.30 (main diastereomer), 52.28 (main diastereomer), 51.96 (secondary diastereomer), 51.63 (main diastereomer), 51.34 (secondary diastereomer), 46.18 (secondary diastereomer), 43.27 (main diastereomer), 29.10 (secondary diastereomer), 28.76 (main diastereomer), 25.64 (secondary diastereomer), 25.19 (main diastereomer), 19.36 (main diastereomer), 18.74 (secondary diastereomer), 15.35 (secondary diastereomer), 9.27 (main diastereomer).

m/z (EI) 332 (M$^+$).

Example A7

$R_1$=1-naphthyl, $R_2$=H, $R_3$=CH$_3$, $R_4$/$R_6$=—(CH$_2$)$_3$—, $R_5$/$R_7$=—(CH$_2$)$_3$—, $R_{17}$=$R_{18}$=H

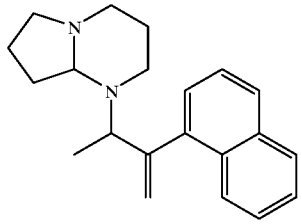

U.V. (CHCl$_3$) max. at 271 nm ($\epsilon$ 26900) and 280 nm (6000).

I.R. (KBr) 1620, 1590, 1570 cm$^{-1}$ (C=C).

$^1$H NMR(CDCl$_3$): 7.77–7.52 (5H, m ArH), 7.42–7.30 (2H, m ArH), 5.54 (0.75H, s, =CH), 5.40 (0.25H, s, =CH), 5.31 (0.75H, s, =CH), 5.29 (0.25H, s, =CH), 4.14 (1H, q, J 6.8 Hz, NCHCH$_3$), 2.87 (3H, m, NCH$_2$), 2.62 (1H, m, NCH), 2.1–1.0 (12H, m, CH$_2$ and CH$_3$).

$^{13}$C NMR (CDCl$_3$): 150.84, 140.43, 133.48, 132.80, 128.11, 127.75, 127.65, 127.54, 127.49, 126.09, 125.80, 125.62, 125.60, 114.86, 82.18 (secondary diastereomer), 81.95 (main diastereomer), 57.22 (secondary diastereomer), 56.33 (main diastereomer), 52.08 (main diastereomer), 51.89 (secondary diastereomer), 51.46 (main diastereomer), 51.28 (secondary diastereomer), 46.00 (secondary diastereomer), 43.41 (main diastereomer), 29.02 (secondary diastereomer), 28.78 (main diastereomer), 25.60 (secondary diastereomer), 25.00 (main diastereomer), 19.39 (main diastereomer), 19.07 (secondary diastereomer), 9.43.

m/z (EI) 306 (M$^+$).

Example A8

$R_1$=2-naphthyl, $R_2$=H, $R_3$=CH$_3$, $R_4$/$R_6$=—(CH$_2$)$_3$—, $R_5$/$R_7$=—(CH$_2$)$_3$—, $R_{17}$=$R_{18}$=H

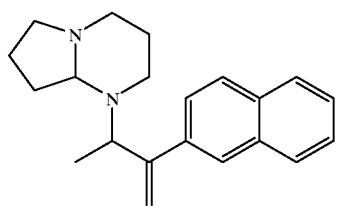

U.V. (CHCl$_3$) max. at 245 ($\epsilon$ 5660).

I.R. (KBr) 1625, 1600, 1570 cm$^{-1}$ (C=C).

$^1$H NMR(CDCl$_3$): 7.83–7.72 (4H, m ArH), 7.60 (1H, m ArH), 7.47–7.24 (2H, m ArH), 5.46 (0.75H, s, =CH), 5.37 (0.25H, s, =CH), 5.25 (075H, s, =CH), 5.20 (0.25H, s, =CH), 4.20 (1H, q, J 6.8 Hz, NCHCH$_3$), 3.01–2.65 (4H, m), 2.18–1.43 (9H, m) and 1.18 (3H, d, J 6.8 Hz, CH$_3$).

$^{13}$C NMR (CDCl$_3$): 150.81, 140.45, 133.49, 132.81, 128.12, 127.53, 125.77, 125.62, 125.48, 114.88, 82.18 (secondary diastereomer), 81.95 (main diastereomer), 56.32, 52.07 (main diastereomer), 51.88 (secondary diastereomer), 51.45 (main diastereomer), 51.28 (secondary diastereomer), 43.40, 29.08 (secondary diastereomer), 28.78 (main diastereomer), 25.41 (secondary diastereomer), 25.00 (main diastereomer), 19.39, 9.45.

m/z (EI) 306 (M$^+$).

Example A9

$R_1$=2-thianthrenyl, $R_2$=H, $R_3$=CH$_3$, $R_4$/$R_6$=—(CH$_2$)$_3$—, $R_5$/$R_7$=—(CH$_2$)$_3$—, $R_{17}$=$R_{18}$=H

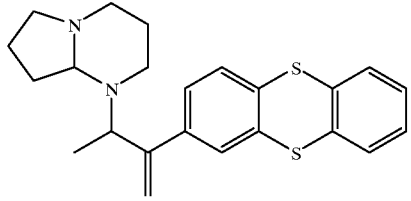

U.V. (CHCl$_3$) max. at 262 nm ($\epsilon$ 29800).

I.R. (KBr) 1625, 1580 cm$^{-1}$ (C=C).

H NMR(CDCl$_3$): 7.47–7.17 (7H, m ArH), 5.32 (0.9H, s, =CH), 5.24 (0.1H, s, =CH), 5.15 (0.9H, s, =CH), 5.11 (0.1H, s, =CH), 4.00 (1H, q, J 6.7 Hz, NCHCH$_3$), 3.03–2.60 (4H, m), 2.26–1.16 (9H, m) and 1.12 (3H, d, J 6.7 Hz, CH$_3$).

$^{13}$C NMR (CDCl$_3$): 149.46, 142.80, 135.82, 135.75, 135.07, 133.80, 128.73, 128.69, 128.37, 127.59, 127.54, 127.10, 126.43, 115.63 (secondary diastereomer), 115.10 (main diastereomer), 82.00 (secondary diastereomer), 81.80 (main diastereomer), 57.37 (secondary diastereomer), 56.25 (main diastereomer), 52.12 (main diastereomer), 51.83 (secondary diastereomer), 51.40 (main diastereomer), 51.21 (secondary diastereomer), 46.65 (secondary diastereomer), 43.26 (main diastereomer), 29.75 (secondary diastereomer), 28.81 (main diastereomer), 25.57 (secondary diastereomer), 25.03 (main diastereomer), 19.38 (main diastereomer), 18.27 (secondary diastereomer), 14.16 (secondary diastereomer), 9.21 (main diastereomer).

m/z (EI) 394 (M$^+$).

Example A10

$R_1$=2-thioxanthyl, $R_2$=H, $R_3$=CH$_3$, $R_4$/$R_6$=—(CH$_2$)$_3$—, $R_5$/$R_7$=—(CH$_2$)$_3$—, $R_{17}$=$R_{18}$=H

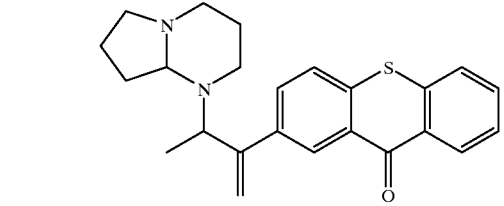

U.V. (CHCl$_3$) max. at 391 nm ($\epsilon$ 4000) and 266 nm (e 28700).

I.R. (KBr) 1640, 1592 cm$^{-1}$ (C=C).

$^1$H NMR(DMSO-d6): 8.49 (1H, d, ArH), 8.47 (1H, d, ArH), 7.89 (1H, dd, ArH), 7.85 (1H, d, ArH), 7.79 (1H, d, ArH), 7.77 (1H, t, ArH), 7.59 (1H, t, ArH), 5.51 (0.9H, s, =CH), 5.45 (0.1H, s, =CH), 5.26 (0.9H, s, =CH), 5.18 (0.1H, s, =CH), 4.19 (1H, q, J 5 Hz, NCHCH$_3$), 2.85–2.80 (4H, m), 2.10–1.19 (9H, m) and 1.16 (3H, d, J 7 Hz, CH$_3$).

$^{13}$C NMR (CDCl$_3$): 178.8, 149.2, 140.6, 136.5, 135.75, 134.9, 132.9, 131.7, 129.1, 128.3, 128.0, 126.8, 126.6, 126.1, 115.3, 81.1, 55.1, 51.5, 50.5, 42.5, 28.0, 24.5, 19.0, 8.5.

m/z (EI) 390 (M$^+$).

Example A11

$R_1$=3,4,5-trimethoxyphenyl, $R_2$=H, $R_3$=$CH_3$, $R_4/R_6$=—$(CH_2)_3$—, $R_5/R_7$=—$(CH_2)_3$—, $R_{17}$=$R_{18}$=H

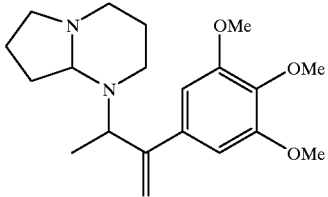

Analysis calculated for $C_{20}H_{30}N_2O_3$: C 69.33; H 8.73; N 8.09. found: C 69.14; H 8.71; N 8.06. U.V. (CHCl$_3$) max at 319 nm (e 1000) and 250 nm (e 7100). I.R. (KBr) 1681, 1578 cm$^{-1}$ (C=C).

$^1$H NMR(CDCl$_3$): 6.65 (1.6H, s, ArH), 6.51 (0.4H, s, ArH), 5.29 (0.8H, s, =CH), 5.24 (0.2H, s, =CH), 5.10 (0.8H, s, =CH), 5.06 (0.2H, s, =CH), 4.04 (1H, q, J 6.8 Hz, NCHCH$_3$), 3.81 (9H, s, OCH$_3$), 2.98–2.79 (3H, m), 2.62 (1H, m), 2.18–1.17 (9H, m) and 1.12 (3H, d, J 6.7 Hz, CH$_3$).

$^{13}$C NMR (CDCl$_3$): 152.8, 150.6, 138.7, 114.2, 104.3, 81.9, 60.7, 56.4, 56.2, 52.1, 51.5, 43.2, 28.8, 25.1, 19.4, 9.3.

m/z (EI) 346 (M$^+$).

Example A12

$R_1$=4-thiomethylphenyl, $R_2$=H, $R_3$=$CH_3$, $R_4/R_6$=—$(CH_2)_3$—, $R_5/R_7$=—$(CH_2)_3$—, $R_{17}$=$R_{18}$=H

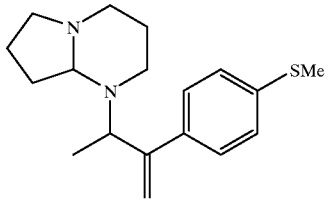

Analysis calculated for $C_{18}H_{26}N_2S$: C 71.48; H 8.66; N 9.26; S 10.60. found: C 71.48; H 8.60; N 8.44; S 10.47.

U.V. (CHCl$_3$) max. at 275 nm (e 14100). I.R. (KBr) 1620, 1593 cm$^{-1}$ (C=C).

$^1$H NMR(CDCl$_3$): 7.43–7.14 (4H, m, ArH), 5.34 (0.75H, s, =CH), 5.22 (0.25H, s, =CH), 5.11 (075H, s, =CH), 5.06 (0.25H, s, =CH), 4.05 (1H, q, J 6.7 Hz, NCHCH$_3$), 3.06–2.59 (4H, m), 2.44 (3H, s, SCH$_3$), 2.17–1.34 (9H, m) and 1.12 (3H, d, J 6.7 Hz, CH$_3$).

$^{13}$C NMR (CDCl$_3$): 149.7, 139.7, 136.8, 127.5, 127.4, 126.6, 126.4, 114.1, 82.0, 56.2, 52.2, 51.6, 51.3, 43.2, 28.7, 25.2, 19.3, 9.2.

m/z (EI) 302 (M$^+$).

Example A13

$R_1$=2-fluorenyl, $R_2$=H, $R_3$=$CH_3$, $R_4/R_6$=—$(CH_2)_3$—, $R_5/R_7$=—$(CH_2)_3$—, $R_{17}$=$R_{18}$=H

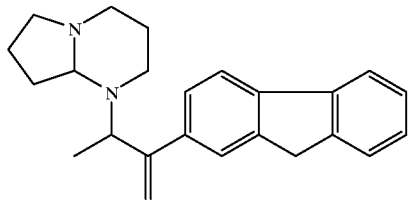

U.V. (CHCl$_3$) max. at 281 nm (e 19500).
I.R. (KBr) 1623, 1611 cm$^{-1}$ (C=C).

$^1$H NMR(CDCl$_3$): 7.78–7.23 (7H, m, ArH), 5.42 (0.75H, s, =CH), 5.32 (0.25H, s, =CH), 5.19 (075H, s, =CH), 5.14 (0.25H, s, =CH), 4.14 (1H, q, J 6.5 Hz, NCHCH$_3$), 3.88 (2H, m, C$_9$ fluorenyl), 3.16–2.87 (3H, m), 2.68 (1H, q, J 5.6 Hz), 2.20–1.24 (9H, m) und 1.17 (3H, d, J 6.7 Hz, CH$_3$).

$^{13}$C NMR (CDCl$_3$): 150.8, 143.5, 143.1, 141.7, 140.7, 126.7, 126.4, 125.8, 1, 125.0, 123.5, 119.8, 119.5, 114.8 (secondary diastereomer), 114.2 (main diastereomer), 82.2 (secondary diastereomer), 82.0 (main diastereomer), 57.3 (secondary diastereomer), 56.5 (main diastereomer), 52.1 (main diastereomer), 52.0 (secondary diastereomer), 51.5 (secondary diastereomer), 51.3 (secondary diastereomer), 45.7 (secondary diastereomer), 43.4 (main diastereomer), 37.0 (C$_9$ fluorenyl), 29.0 (secondary diastereomer), 28.8 (main diastereomer), 25.7 (secondary diastereomer), 25.1 (main diastereomer), 19.4, 9.5.

m/z (EI) 344 (M$^+$).

Example A14

$R_1$=phenyl, $R_2$=H, $R_3$=$CH_3$, $R_4/R_6$=—$(CH_2)_3$—, $R_5/R_7$=—$(CH_2)_3$—, $R_{17}$=H, $R_{18}$=$CH_3$

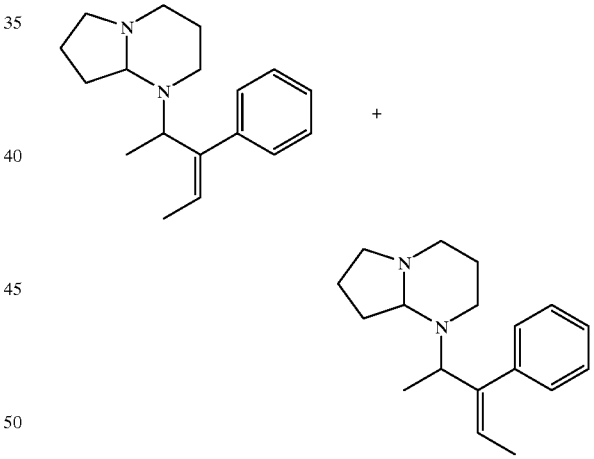

$^1$H NMR (CDCl$_3$): 7.31–7.10 (5H, m ArH), 5.70–5.50 (1H, m, =CH), 3.80 (1H, m, NCHCH$_3$), 2.94 (3H, m, NCH$_2$), 2.61 (1H, m, NCH), 2.1–1.0 (15H, m, CH$_2$ and CH$_3$).

Use Examples B: Base catalysis with monomeric compounds

Examples B1–B4

UV-initiated Michael addition.

$7.4 \cdot 10^{-5}$ mol of photoinitiator (latent amidine base) are dissolved in a mixture of dimethyl malonate and n-butyl acrylate (1:1, 200 mg corresponding to $7.4 \cdot 10^{-4}$ mol) in a quartz vessel. The mixture is irradiated with a high-pressure mercury lamp (200 W) from a distance of 30 cm. The conversion is monitored as a function of time.

The results are set out in Table 1.

TABLE 1

| Example | Initiator from Example | Conversion in % after exposure time of | | | | | | |
|---|---|---|---|---|---|---|---|---|
| | | 0 min | 10 min | 20 min | 30 min | 40 min | 60 min | 120 min |
| B1 | A1 | 0 | — | 6 | — | 38 | 68 | 100 |
| B2 | A2 | 0 | — | 8 | — | 35 | 58 | 94 |
| B3 | A4 | 0 | — | 16 | — | 50 | 75 | 100 |
| B4 | A5 | 0 | 19 | 64 | 91 | 100 | | |
| B5 | A6 | 0 | 31 | 67 | 81 | 89 | 94 | 100 |
| B6 | A8 | 0 | 40 | 94 | 100 | | | |
| B7 | A9 | 0 | 56 | 89 | 94 | 100 | | |
| B8 | A10 | 0 | 74 | 98 | 100 | | | |
| B9 | A11 | 0 | 7 | 60 | 88 | 100 | | |
| B10 | A12 | 0 | 18 | 33 | 61 | 83 | 100 | |
| B11 | A13 | 0 | 11 | 76 | 94 | 100 | | |

Use Examples C: Base catalysis with oligomer/polymer compounds

Example C1

Preparation of a urethane acrylate based on isophorone diisocyanate and 4-hydroxybutyl acrylate.

The reaction is carried out under a nitrogen atmosphere and all commercial chemicals used are employed without further purification.

1566.8 g (13.78 mol of NCO) of isophorone diisocyanate, 2.3 g of dibutyltin dilaurate, 2.3 g of 2,5-di-tert.-butyl-p-cresol and 802.8 g of butyl acetate are charged to a three-necked flask with condenser and dropping device. Dry nitrogen is bubbled through the reaction mixture and the temperature is slowly raised to 60° C. 1987 g (13.78 mol) of 4-hydroxybutyl acrylate are added, during which the reaction solution warms slowly to 80° C. The temperature is held at 80° C. and the dropping device is flushed with butyl acetate (86.6 g). The reaction is monitored by titration of the remaining amount of isocyanate, and is over when the isocyanate content is below 0.2% based on the solids content. The reaction product obtained has the following physical properties:

Residual 4-hydroxybutyl acrylate: <0.002% based on solids (HPLC analysis),
Colour: <<Gardner 1,
Viscosity: 43 cPa s (20° C.),
Solids content: 79,3% (1 hour at 140° C.),
GPC data (polystyrene standard): $M_n$ 778, $M_w$ 796, d=1.02.

Preparation of a malonate polyester

The reaction is carried out under a nitrogen atmosphere and all commercial chemicals used are employed without further purification.

In a reaction vessel with stirrer and condenser 1045 g of 1,5-pentanediol, 1377.4 g of diethyl malonate and 242.1 g of xylene are carefully refluxed, The maximum temperature of the reaction mixture is 196° C. while the temperature at the head of the condenser is held at 79° C. In this way 862 g of ethanol, corresponding to a conversion of 97.7%, are distilled off. Then xylene is stripped off in vacuo at a temperature of 200° C. The resulting polymer has a solids content of 98.6%, a viscosity of 2710 mPa s and an acid number of 0.3 mg of KOH/g based on the solids content. $M_n$ is 1838, $M_w$ is 3186, the colour is 175 on the APHA scale ("Hazen colour number"—ISO 6271 of the American Health Association).

Curing with UV light ($6.4 \times 10^{-5}$ mol) of the photoinitiator from Example A5 are dissolved in a 1.3:1 mixture of the above-described urethane acrylate and the malonate polyester (total amount 400 mg). A film 50 μm thick is drawn out onto a glass plate and is exposed using a high-pressure mercury lamp (200 W) at a distance of 30 cm. The polymer film is tack-free after 120 minutes.

What is claimed is:

1. An organic compound having a molecular weight of less than 1000, comprising at least one structural unit of the formula (I)

(I)

in which
   $R_1$ is an aromatic or heteroaromatic radical capable of absorbing light in the wavelength range from 200 to 650 nm and in so doing brings about cleavage of the adjacent carbon-nitrogen bond.

2. An organic compound according to claim 1 wherein the structural unit of the formula (I) comprises compounds of the formula (II)

(II)

in which
   $R_1$ is an aromatic or heteroaromatic radical which is capable of absorbing light in the wavelength range from 200 to 650 nm and in doing so brings about cleavage of the adjacent carbon-nitrogen bond;
   $R_2$ and $R_3$ independently of one another are hydrogen, $C_1$–$C_{18}$alkyl, $C_3$–$C_{18}$alkenyl, $C_3$–$C_{18}$alkynyl or phenyl and, if $R_2$ is hydrogen or $C_1$–$C_{18}$alkyl, $R_3$ is additionally a group —CO—$R_{14}$ in which $R_{14}$ is $C_1$–$C_{18}$alkyl or phenyl;
   $R_5$ is $C_1$–$C_{18}$alkyl or $NR_{15}R_{16}$;
   $R_4$, $R_6$, $R_7$, $R_{15}$ and $R_{16}$ independently of one another are hydrogen or $C_1$–$C_{18}$alkyl; or
   $R_4$ and $R_6$ together form a $C_2$–$C_{12}$alkylene bridge or
   $R_5$ and $R_7$, independently of $R_4$ and $R_6$, together form a $C_2$–$C_{12}$alkylene bridge or, if $R_5$ is $NR_{15}R_{16}$, $R_{16}$ and $R_7$ together form a $C_2$–$C_{12}$alkylene bridge;
   $R_{17}$ is hydrogen or $C_1$–$C_{18}$alkyl;
   $R_{18}$ is hydrogen, $C_1$–$C_{18}$alkyl or phenyl substituted by $C_1$–$C_{18}$alkyl, vinyl, $C_3$–$C_{18}$alkenyl, $C_3$–$C_{18}$alkynyl, $C_1$–$C_{18}$haloalkyl, phenyl, $NO_2$, OH, ON, $OR_{10}$, $SR_{10}$, $C(O)R_{11}$, $C(O)OR_{12}$ or halogen; and
   $R_{10}$, $R_{11}$, and $R_{12}$ are hydrogen or $C_1$–$C_{18}$alkyl.

3. An organic compound according to claim 2, wherein $R_2$ and $R_3$ independently of one another are hydrogen or $C_1$–$C_6$alkyl.

4. An organic compound according to claim 2, wherein $R_4$ and $R_6$ together form a $C_2$–$C_6$alkylene bridge.

5. An organic compound according to claim 2, wherein $R_5$ and $R_7$ form a $C_2$–$C_6$alkylene bridge or, if $R_5$ is $NR_{15}R_{16}$, $R_{16}$ and $R_7$ together form a $C_2$–$C_6$alkylene bridge.

6. A process for preparing a compound of the formula (II) according to claim 2, which comprises reacting a compound of the formula (V)

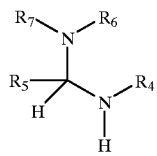
(V)

in which the radicals $R_4$, $R_5$, $R_6$ and $R_7$ are as defined in claim 2, with a compound of the formula (VI)

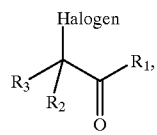
(IV)

in which $R_1$, $R_2$ and $R_3$ are as defined in claim 2 and Halogen is F, Cl, Br or I, and, in a second step, conducting a Wittig reaction with the reaction product thus obtained using a phosphonium salt of the formula VII

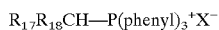
(VII), in which $R_{17}$ and $R_{18}$ are as defined in claim 2 and X is F, Cl, BR, I or tetrafluoroborate.

7. A process for preparing a compound of the formula (VII),

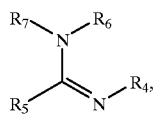
(VII)

in which the radicals $R_4$, $R_5$, $R_6$ and $R_7$ are as defined in claim 2, which comprises exposing a compound of the formula (II)

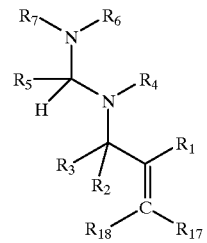
(II)

according to claim 2
to light having a wavelength from 200 nm to 650 nm.

8. An organic compound according to claim 1, wherein $R_1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphto[2,3-b] thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or substituted one or more times by $C_1$–$C_{18}$alkyl, $C_3$–$C_{18}$alkenyl, $C_3$–$C18$alkynyl, $C_1$–$C_{18}$haloalkyl, $NO_2$, $NR_8R_9$, $N_3$, OH, CN, $OR_{10}$, $SR_{10}$, $C(O)R_{11}$, $C(O)OR_{12}$ or halogen, or $R_1$ is a radical of the formulae A or B

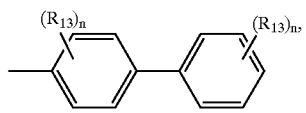
(A)

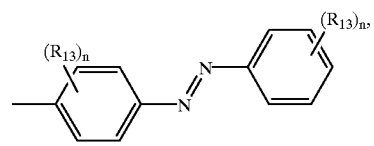
(B)

$R_8$, $R_9$, $R_{10}$, $R_{11}$ and $R_{12}$ are hydrogen or $C_1$–$C_{18}$alkyl;

$R_{13}$ is $C_1$–$C_{18}$alkyl, $C_2$–$C_{18}$alkenyl, $C_2$–$C_{18}$alkynyl, $C_1$–$C_{18}$haloalkyl, $NO_2$, $NR_8R_9$, OH, ON, $OR_{10}$, $SR_{10}$, $C(O)R_{11}$, $C(O)OR_{12}$ or halogen; and n is 0 or a number 1, 2 or 3.

9. An organic compound of the formula (II) according to claim 8, wherein $R_1$ is phenyl or naphthyl, the phenyl and naphthyl radicals being unsubstituted or being substituted one or more times by CN, $NR_8R_9$, $N_3$, $NO_2$, $CF_3$, $SR_{10}$ or $OR_{10}$ or $R_1$ is thianthrenyl, fluorenyl or thioxanthyl, or $R_1$ is a radical of the formula A or B

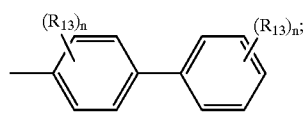

n is 0 and the radicals $R_8$, $R_9$ and $R_{10}$ are hydrogen or $C_1$–$C_6$alkyl;
$R_2$ and $R_3$ are hydrogen or $C_1$–$C_6$alkyl;
$R_4$ and $R_6$ together form a $C_2$–$C_6$alkylene bridge;
$R_5$ and $R_7$ together form a $C_2$–$C_6$alkylene bridge;
$R_{17}$ is hydrogen; and
$R_{18}$ is hydrogen or $C_1$–$C_4$alkyl.

10. A process for preparing a compound having the structural unit of the formula (I) according to claim 1, which comprises reacting, in a first step, a compound having a structural unit of the formula (III)

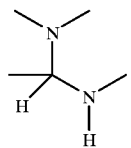

with a compound having a structural unit of the formula IV

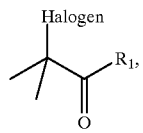

in which
Halogen is F, Cl, Br or I and $R_1$ is as defined in claim 1 and, in a second step, carrying out a Wittig reaction, using a phosphonium salt, with the reaction product thus obtained.

11. A composition comprising
A) at least one compound having a structural unit of the formula (I) according to claim 1 and
B) at least one organic compound capable of a base-catalysed addition or substitution reaction.

12. A composition according to claim 11, wherein component (B) is an anionically polymerizable or crosslinkable organic material.

13. A composition according to claim 11, wherein component (B) is one of the following systems:
a) Acrylate copolymers having alkoxysilane or alkoxysiloxane side groups;
b) Two-component systems comprising hydroxyl-containing polyacrylates, polyesters or polyethers and aliphatic or aromatic polyisocyanates;
c) Two-component systems comprising functional polyacrylates and a polyepoxide, where the polyacrylate comprises carboxyl, anhydride groups;
d) Two-component systems comprising fluorine-modified or silicone-modified hydroxyl-containing polyacrylates, polyesters or polyethers and aliphatic or aromatic polyisocyanates;
e) Two-component systems comprising (poly)ketimines and aliphatic or aromatic polyisocyanates;
f) Two-component systems comprising (poly)ketimines and unsaturated acrylate resins or acetoacetate resins or methyl α-acrylamidomethylglycolate;
h) Two-component systems comprising (poly)oxazolidines and polyacrylates containing anyhydride groups, or unsaturated acrylate resins or polyisocyanates;
i) Two-component systems comprising epoxy-functional polyacrylates and carboxyl-containing or amino-containing polyacrylates;
l) Poly(allyl glycidyl ether);
m) Two-component systems comprising a (poly)alcohol and a (poly)isocyanate;
n) Two-component systems comprising an α,β-ethylenically unsaturated carbonyl compound and a polymer comprising activated $CH_2$ groups.

14. A composition according to claim 11, wherein the component B) is an epoxy resin or a mixture of different epoxy resins.

15. A composition according to claim 11, wherein component A) is present in an amount of from 0.01 to 10% by weight based on component B).

16. A composition according to claim 11, which additionally comprises a sensitizer selected from the group consisting of thioxanthones, oxazines, acridines, phenazines and rhodamines.

17. A method of implementing base-catalysed reactions, which comprises subjecting a composition according to claim 11 to irradiation with light having a wavelength of from 200 nm to 650 nm.

18. A method according to claim 17, wherein heating is carried out during or after exposure to light.

19. A method according to claim 17 for producing coatings, moulding compositions or photostructured layers.

20. A polymerized or crosslinked composition prepared according to the method of claim 17.

21. A coated substrate which has been coated on at least one surface with a composition according to claim 11.

* * * * *